United States Patent [19]
Stone

[11] Patent Number: 6,063,120
[45] Date of Patent: May 16, 2000

[54] ANTERIOR CRUCIATE LIGAMENT HETEROGRAFT

[76] Inventor: Kevin R. Stone, 3727 Buchanan St., San Francisco, Calif. 94125

[21] Appl. No.: 09/022,658

[22] Filed: Feb. 12, 1998

Related U.S. Application Data

[62] Division of application No. 08/529,199, Sep. 15, 1995, abandoned.

[51] Int. Cl.⁷ ........................................................ A61F 2/08
[52] U.S. Cl. .................................. 623/13; 623/16; 623/66
[58] Field of Search .................................. 623/11, 13, 12, 623/16, 18, 66; 514/21, 2; 424/95, 423; 427/2

[56] References Cited

U.S. PATENT DOCUMENTS

| | | |
|---|---|---|
| 4,034,418 | 7/1977 | Jackson et al. . |
| 4,344,193 | 8/1982 | Kenny . |
| 4,400,833 | 8/1983 | Kurland . |
| 4,502,161 | 3/1985 | Wall . |
| 4,597,266 | 7/1986 | Entrekin . |
| 4,609,627 | 9/1986 | Goldstein . |
| 4,627,853 | 12/1986 | Campbell et al. . |
| 4,642,120 | 2/1987 | Nevo et al. . |
| 4,678,470 | 7/1987 | Nashef et al. . |
| 4,755,593 | 7/1988 | Lauren . |
| 4,776,853 | 10/1988 | Klement et al. . |
| 4,789,663 | 12/1988 | Wallace et al. . |
| 4,801,299 | 1/1989 | Brendel et al. . |
| 4,846,835 | 7/1989 | Grande . |
| 4,880,429 | 11/1989 | Stone . |
| 4,932,973 | 6/1990 | Gendler . |
| 5,007,934 | 4/1991 | Stone . |
| 5,067,962 | 11/1991 | Campbell et al. . |
| 5,071,741 | 12/1991 | Brockbank . |
| 5,078,744 | 1/1992 | Chvapil . |
| 5,092,894 | 3/1992 | Kenny . |
| 5,116,374 | 5/1992 | Stone . |
| 5,131,850 | 7/1992 | Brockbank . |
| 5,158,574 | 10/1992 | Stone . |
| 5,160,313 | 11/1992 | Carpenter et al. . |
| 5,171,273 | 12/1992 | Silver et al. . |
| 5,171,322 | 12/1992 | Kenny . |
| 5,171,660 | 12/1992 | Carpenter et al. . |
| 5,192,312 | 3/1993 | Orton . |
| 5,216,126 | 6/1993 | Cox et al. . |
| 5,306,304 | 4/1994 | Gendler . |
| 5,306,311 | 4/1994 | Stone et al. . |
| 5,358,525 | 10/1994 | Fox et al. . |
| 5,507,810 | 4/1996 | Prewett et al. . |
| 5,613,982 | 3/1997 | Goldstein . |

FOREIGN PATENT DOCUMENTS

| | | |
|---|---|---|
| WO 84/03036 | 8/1984 | WIPO . |
| WO 95/26740 | 10/1995 | WIPO . |
| WO 95/28412 | 10/1995 | WIPO . |
| WO 95/33828 | 12/1995 | WIPO . |

OTHER PUBLICATIONS

Rodrigo et al., *Clinical Orthopedics and Related Research*, 134:342–349 (1978).
Sengupta et al., *The Journal of Bone and Joint Surgery*, 56B:167–177 (1974).
Webber et al., *Journal of Orthopedic Research*, 3:36–42 (1985).
Rubak et al., *Acta Orthop. Scand*, 53:181–186 (1982).
Engkvist, Ove, *Scand. J. Plast. Reconstr. Surg.*, 13:361–369 (1982).
Collins et al., Xenotransplantation, Characterization of Porcine Endothelial Cell Determinants Recognized by Human Natural Antibodies, 1:36–46 (1994).
Satake et al., Xenotransplanation, Limited Specificity of Xenoantibodies In Diabetic Patients Transplanted With Fetal Porcine Islet Cell Clusters. Main Antibody Reactivity Against α–linked Galactose–Containing Epitopes, 1:89–101 (1994).
LaVecchio et al., Transplantation, Enzymatic Removal of Alpha–Galactosyl Epitopes From Porcine Endothelial Cells Diminishes The Cytotoxic Effect of Natural Antibodies, 60:841–847.
Cotterell et al., Transplantation, The Humoral Immune Response in Humans Following Cross–Perfusion of Porcine Organs, 60:861–868 (1955).
Galili, Immunology Today, 14:480–482 (1993).
Elves et al., An Investigation Into The Immunogenicity of Various Components of Osteoarticular Grafts, *The British Journal of Experimental Pathology*, 55:344–351 (1974).

*Primary Examiner*—David J. Isabella
*Attorney, Agent, or Firm*—McDermott, Will & Emery

[57] ABSTRACT

The invention provides an article of manufacture comprising a substantially non-immunogenic ligament or tendon heterografts for implantation into humans. The invention further provides a method for preparing an ligament heterograft by removing at least a portion of an ligament from a non-human animal to provide a heterograft; washing the heterograft in saline and alcohol; subjecting the heterograft to at least one treatment selected from the group consisting of exposure to ultraviolet radiation, immersion in alcohol, ozonation, freeze/thaw cycling, and optionally to chemical crosslinking. In accordance with the invention the heterograft has substantially the same mechanical properties as the native xenogeneic ligament.

20 Claims, No Drawings

ANTERIOR CRUCIATE LIGAMENT HETEROGRAFT

This application is a division of application Ser. No. 08/529,199, filed Sep. 15, 1995 now abandoned.

The present invention relates to the field of surgical repair of injuries of the anterior cruciate ligament in the human knee using a substantially immunologically compatible ligament or tendon from a non-human animal to replace the damaged human anterior cruciate ligament.

BACKGROUND OF THE INVENTION

The anterior cruciate ligament of the knee (hereinafter the ACL) functions to resist anterior displacement of the tibia from the femur at all flexion positions. The ACL also resists hyperextension and contributes to rotational stability of the fully extended knee during internal and external tibial rotation. The ACL may play a role in proprioception. Structurally, the ACL attaches to a depression in the front of the intercondyloid eminence of the tibia extending postero-superiorly to the medial wall of the lateral femoral condyle.

Partial or complete tears of the ACL are very common, comprising about 30,000 outpatient procedures in the U.S. each year. The preferred treatment of the torn ACL is ligament reconstruction, using a bone-ligament-bone autograft. Cruciate ligament reconstruction has the advantage of immediate stability and a potential for immediate vigorous rehabilitation. However, the disadvantages to ACL reconstruction are significant: for example, normal anatomy is disrupted when the patellar tendon or hamstring tendons are used for the reconstruction; placement of intraarticular hardware is required for ligament fixation; and anterior knee pain frequently occurs. Moreover, recent reviews of cruciate ligament reconstruction indicate an increased risk of degenerative arthritis with intraarticular ACL reconstruction in large groups of patients.

A second method of treating ACL injuries, referred to as "primary repair", involves suturing the torn structure back into place. Primary ACL repair has the potential advantages of a limited arthroscopic approach, minimal disruption of normal anatomy, and an out-patient procedure under a local anesthetic. The potential disadvantage of primary cruciate ligament repair is the perception that over the long term ACL repairs do not provide stability in a sufficient number of patients, and that subsequent reconstruction may be required at a later date. The success rate of anterior cruciate ligament repair has generally hovered in the 60% to 70% range.

Much of the structure and many of the properties of original tissues may be retained in transplants through use of xenogeneic or heterograft materials, that is, tissue from a different species than the graft recipient. For example, tendons or ligaments from cows or other animals are covered with a synthetic mesh and transplanted into a heterologous host in U.S. Pat. No. 4,400,833. Flat tissues such as pig pericardia are also disclosed as being suitable for heterologous transplantation in U.S. Pat. No. 4,400,833. Bovine peritoneum fabricated into a biomaterial suitable for prosthetic heart valves, vascular grafts, burn and other wound dressings is disclosed in U.S. Pat. No. 4,755,593. Bovine, ovine, or porcine blood vessel heterografts are disclosed in WO 84/03036. However, none of these disclosures describe the use of a xenograft for ACL replacement.

Xenograft materials must be chemically treated to reduce immunogenicity prior to implantation into a recipient. For example, glutaraldehyde is used to cross-link or "tan" xenograft tissue in order to reduce its antigenicity, as described in detail in U.S. Pat. No. 4,755,593. Other agents such as aliphatic and aromatic diamine compounds may provide additional crosslinking through the sidechain carboxyl groups of aspartic and glutamic acid residues of the collagen polypeptide. Glutaraldehyde and diamine tanning also increases the stability of the xenograft tissue.

Xenograft tissues may also be subjected to various physical treatments in preparation for implantation. For example, U.S. Pat. No. 4,755,593 discloses subjecting xenograft tissue to mechanical strain by stretching to produce a thinner and stiffer biomaterial for grafting. Tissue for allograft transplantation is commonly cryopreserved to optimize cell viability during storage, as disclosed, for example, in U.S. Pat. No. 5,071,741; U.S. Pat. No. 5,131,850; U.S. Pat. No. 5,160,313; and U.S. Pat. No. 5,171,660. U.S. Pat. No. 5,071,741 discloses that freezing tissues causes mechanical injuries to cells therein because of extracellular or intracellular ice crystal formation and osmotic dehydration.

SUMMARY OF THE INVENTION

The present invention provides a substantially non-immunogenic ligament or tendon heterograft for implantation into a human in need of ACL repair. The invention further provides methods for processing xenogeneic ligaments with reduced immunogenicity but with substantially native elasticity and load-bearing capabilities for heterografting into humans. The method of the invention, which may include, alone or in combination, treatment with radiation, one or more cycles of freezing and thawing, treatment with a chemical cross-linking agent, treatment with alcohol, or ozonation, provides a heterograft having substantially the same mechanical properties of a native ligament.

In one embodiment, the invention provides an article of manufacture comprising a substantially non-immunogenic ligament heterograft for implantation into a human.

In another embodiment, the invention provides a method of preparing an ligament heterograft for implantation into a human, which comprises removing at least a portion of a ligament from a knee joint of a non-human animal to provide a heterograft; washing the heterograft in water and alcohol; and subjecting the heterograft to at least one treatment selected from the group consisting of exposure to ultraviolet radiation, immersion in alcohol, ozonation, and freeze/thaw cycling, whereby the heterograft has adequate mechanical properties to perform as a substitute ligament.

DETAILED DESCRIPTION OF THE PREFERRED EMBODIMENTS

The xenogeneic ligament or tendon heterograft produced in accordance with the method of the invention is substantially non-immunogenic, while generally maintaining the mechanical properties of a native ligament. While the ligament may undergo some shrinkage during processing, a xenogeneic ligament heterograft prepared in accordance with the invention will have the general appearance of a native ligament. The xenogeneic ligament heterograft may also be cut into segments, each of which may be implanted into the knee of a recipient as set forth below.

The invention provides, in one embodiment, a method for preparing or processing a xenogeneic ligament or tendon for engraftment into humans. As defined herein, "xenogeneic" means originate from any non-human animal. Thus ligament or tendon may be harvested from any non-human animal to prepare the heterografts of the invention. Ligament from transgenic non-human animals or from genetically altered non-human animals may also be used as heterografts in accordance with the present invention. Preferably, bovine, ovine, or porcine knee joints serve as sources of the ligament used to prepare the heterografts. More preferably, immature pig, calf or lamb knee joints are the sources of the ligament, since the tissue of younger animals may be inherently more elastic and engraftable than that of older animals. Most preferably, the age of the source animal is between six and eighteen months at time of slaughter. Additionally, the patellar tendon, the anterior or posterior cruciate ligaments, the Achilles tendon, or the hamstring tendons may be harvested from the animal source and used as a donor ligament.

In the first step of the method of the invention, an intact ligament or tendon is removed from the knee of a non-human animal. The joint which serves as the source of the ligament should be collected from freshly killed animals and preferably immediately placed in a suitable sterile isotonic or other tissue preserving solution. Harvesting of the joints should occur as soon as possible after slaughter of the animal and should be performed in the cold, i.e., in the approximate range 5–20° C., to minimize enzymatic and/or bacterial degradation of the ligament tissue. The ligament are harvested from the joints in the cold, under strict sterile technique. The joint is opened by standard surgical technique. Preferably, the ligament is harvested with a block of bone attached to one or both ends, although in some forms of the invention the ligament alone is harvested. In one form of the invention, a block of bone representing a substantially cylindrical plug of approximately forty millimeters in diameter by forty millimeters in depth may be left attached to the ligament. The ligament is carefully identified and dissected free of adhering tissue, thereby forming the heterograft.

The heterograft is then washed in about ten volumes of sterile cold water to remove residual blood proteins and water soluble materials. The heterograft is then immersed in alcohol at room temperature for about five minutes, to sterilize the tissue and to remove non-collagenous materials. After alcohol immersion, the heterograft may be directly implanted into a knee. Alternatively, the heterograft may be subjected to at least one of the treatments set forth below. When more than one treatment is applied to the heterograft, the treatments may occur in any order. In one embodiment of the method of the invention, the heterograft may be treated by exposure to radiation, for example, by being placed in an ultraviolet radiation sterilizer such as the Stragene™ Model 2400, for about fifteen minutes. In another embodiment, the heterograft may be treated by again being placed in an alcohol solution. Any alcohol solution may be used to perform this treatment. Preferably, the heterograft is placed in a 70% solution of isopropanol at room temperature. In another embodiment, the heterograft may be subjected to ozonation.

In another embodiment, the heterograft may be treated by freeze/thaw cycling.

For example, the heterograft may be frozen using any method of freezing, so long as the heterograft is completely frozen, i.e., no interior warm spots remain which contain unfrozen tissue. Preferably, the heterograft is dipped into liquid nitrogen for about five minutes to perform this step of the method. More preferably, the heterograft is frozen slowly by placing it in a freezer. In the next step of the freeze/thaw cycling treatment, the heterograft is thawed by immersion in an isotonic saline bath at room temperature (about 25° C.) for about ten minutes. No external heat or radiation source is used, in order to minimize fiber degradation.

The heterograft may optionally be exposed to a chemical agent to tan or crosslink the proteins within the interstitial matrix, to further diminish or reduce the immunogenic determinants present in the heterograft. Any tanning or crosslinking agent may be used for this treatment, and more than one crosslinking step may be performed or more than one crosslinking agent may be used in order to ensure complete crosslinking and thus optimally reduce the immunogenicity of the heterograft. For example, aldehydes such as glutaraldehyde, formaldehyde, adipic dialdehyde, and the like, may be used to crosslink the collagen within the interstitial matrix of the heterograft in accordance with the method of the invention. Other suitable crosslinking agents include aliphatic and aromatic diamines, carbodiimides, diisocyanates, and the like. When glutaraldehyde is used as the crosslinking agent, for example, the heterograft may be placed in a buffered solution containing about 0.05 to about 5.0% glutaraldehyde and having a pH of about 7.4. Any suitable buffer may be used, such as phosphate buffered saline or trishydroxymethylaminomethane, and the like, so long as it is possible to maintain control over the pH of the solution for the duration of the crosslinking reaction, which may be from one to fourteen days, and preferably from three to five days. The crosslinking reaction should continue until the immunogenic determinants are substantially removed from the xenogeneic tissue, but the reaction should be terminated prior to significant alterations of the mechanical properties of the heterograft. When diamines are also used as crosslinking agents, the glutaraldehyde crosslinking should occur after the diamine crosslinking, so that any unreacted diamines are capped. After the crosslinking reactions have proceeded to completion as described above, the heterograft should be rinsed to remove residual chemicals, and 0.01–0.05 M glycine may be added to cap any unreacted aldehyde groups which remain.

Prior to treatment, the outer surface of the heterograft may optionally be pierced to increase permeability to agents used to render the heterograft substantially non-immunogenic. A sterile surgical needle such as an 18 gauge needle may be used to perform this piercing step, or, alternatively a comb-like apparatus containing a plurality of needles may be used. The piercing may be performed with various patterns, and with various pierce-to-pierce spacings, in order to establish a desired access to the interior of the heterograft. Piercing may also be performed with a laser. In one form of the invention, one or more straight lines of punctures about three millimeters apart are established circumferentially in the outer surface of the heterograft.

Prior to implantation, the ligament or tendon heterograft of the invention may be treated with limited digestion by proteolytic enzymes such as ficin or trypsin to increase tissue flexibility, or with glycosidases to remove surface carbohydrate moieties, or coated with anticalcification agents, antithrombotic coatings, antibiotics, growth factors, or other drugs which may enhance the incorporation of the heterograft into the recipient knee joint. The ligament heterograft of the invention may be further sterilized using known methods, for example, with additional glutaraldehyde or formaldehyde treatment, ethylene oxide sterilization, propylene oxide sterilization, or the like. The heterograft may be stored frozen until required for use.

The ligament or tendon heterograft of the invention, or a segment thereof, may be implanted into a damaged human knee joint by those of skill in the art using known arthroscopic surgical techniques. Specific instruments for performing arthroscopic techniques are known to those of skill in the art, which ensure accurate and reproducible placement of ligament implants. Initially, complete diagnostic arthroscopy of the knee joint is accomplished using known methods. The irreparably damaged ligament is removed with a surgical shaver. The anatomic insertion sites for the ligament are identified and drilled to accommodate a 10 millimeter bone plug. The xenogeneic ligament is brought through the drill holes and affixed with interference screws. Routine closure is performed.

Those of skill in the art will recognize that the invention may be embodied in other specific forms without departing from the spirit or essential characteristics thereof. The presently described embodiments are therefore to be considered in all respects as illustrative and not restrictive, the scope of the invention being indicated by the appended claims rather than by the foregoing description, and all variations of the invention which are encompassed within the meaning and range of equivalency of the claims are therefor intended to be embraced therein.

What is claimed is:

1. An article of manufacture comprising a substantially non-immunogenic glycosidase-treated ligament heterograft for implantation into a human, produced by the process of
   a. removing at least a portion of a ligament from a non-human animal to provide a heterograft;
   b. washing the heterograft in water and alcohol;
   c. subjecting the heterograft to at least one treatment selected from the group consisting of exposure to ultraviolet radiation, immersion in alcohol, ozonation, and freeze/thaw cycling; and
   d. digesting the heterograft with a glycosidase to remove surface carbohydrate moieties,
whereby the heterograft has substantially the same mechanical properties as a corresponding portion of a native ligament.

2. The article of manufacture according to claim 1 wherein the heterograft has a plurality of punctures for increasing permeability to agents and enzymes.

3. The article of manufacture according to claim 1 wherein the non-immunogenic glycosidase-treated ligament heterograft is a second enzyme-treated heterograft.

4. The article of manufacture of claim 3 wherein the second enzyme is selected from the group consisting of ficin and trypsin.

5. The article of manufacture of claim 1, further comprising one or more agents selected from the group consisting of anticalcification agents, antithrombotic agents, antibiotics, and growth factors.

6. The article of manufacture of claim 1 wherein the heterograft is sterilized.

7. The article of manufacture of claim 6, wherein the heterograft is sterilized with an agent selected from the group consisting of glutaraldehyde, formaldehyde, ethylene oxide, and propylene oxide.

8. The article of manufacture of claim 1, wherein the portion is a segment of the ligament.

9. The article of manufacture of claim 1, wherein the portion of the ligament has a first block of bone attached to a first end thereof.

10. The article of manufacture of claim 9, wherein the portion of the ligament has a second block of bone affixed to a second end thereof opposite the first end.

11. The article of manufacture of claim 1, wherein the the heterograft has undergone freeze/thaw cycling.

12. An article of manufacture comprising a substantially non-immunogenic glycosidase-treated ligament or tendon heterograft for implantation into a human, whereby the heterograft has substantially the same mechanical properties as a corresponding portion of a native ligament.

13. The article of manufacture of claim 12 wherein said heterograft includes a first block of bone attached to one end thereof.

14. The article of manufacture of claim 13 wherein said heterograft includes a second block of bone affixed to the end thereof opposite said one end.

15. The article of manufacture of claim 12, wherein the heterograft is a processed native xenogeneic ligament.

16. The article of manufacture of claim 15 wherein said heterograft includes a first block of bone attached to one end thereof.

17. The article of manufacture of claim 16 wherein said heterograft includes a second block of bone affixed to the end thereof opposite said one end.

18. The article of manufacture of claim 12, wherein the heterograft is a segment of a processed native xenogeneic ligament.

19. The article of manufacture of claim 18 wherein said heterograft includes a first block of bone attached to one end thereof.

20. The article of manufacture of claim 19 wherein said heterograft includes a second block of bone affixed to the end thereof opposite said one end.

* * * * *